(12) United States Patent
Chen (10) Patent No.: US 10,537,583 B2
(45) Date of Patent: Jan. 21, 2020

(54) ORAL FORMULATION OF A-NOR-5α ANDROSTANE COMPOUND

(71) Applicant: Yajun Chen, Shanghai (CN)

(72) Inventor: Yajun Chen, Shanghai (CN)

( * ) Notice: Subject to any disclaimer, the term of this patent is extended or adjusted under 35 U.S.C. 154(b) by 0 days.

(21) Appl. No.: 15/515,555

(22) PCT Filed: Sep. 28, 2015

(86) PCT No.: PCT/CN2015/090951
§ 371 (c)(1),
(2) Date: Mar. 29, 2017

(87) PCT Pub. No.: WO2016/050193
PCT Pub. Date: Apr. 7, 2016

(65) Prior Publication Data
US 2017/0216313 A1    Aug. 3, 2017

(30) Foreign Application Priority Data

Sep. 29, 2014  (CN) .......................... 2014 1 0520235

(51) Int. Cl.
*A61K 31/569*   (2006.01)
*A61K 9/00*   (2006.01)
*A61K 9/20*   (2006.01)

(52) U.S. Cl.
CPC .......... *A61K 31/569* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01)

(58) Field of Classification Search
CPC .. A61K 31/569; A61K 9/2054; A61K 9/2027; A61K 9/2018; A61K 9/2013; A61K 9/2009; A61K 9/0053; A61K 9/2059; A61K 9/20; A61K 47/30; A61K 47/26; A61K 47/14; A61K 47/38
See application file for complete search history.

(56) References Cited

U.S. PATENT DOCUMENTS

2003/0180352 A1*  9/2003  Patel ................... A61K 9/1617
424/465

FOREIGN PATENT DOCUMENTS

| CN | 1313082 A | | 9/2001 | | |
|---|---|---|---|---|---|
| CN | 1331082 A | * | 1/2002 | | |
| CN | 1634078 A | | 7/2005 | | |
| CN | 101939009 A | * | 1/2011 | ............ | C07J 1/0048 |
| CN | 102218069 A | * | 10/2011 | ........... | A61K 31/568 |
| GB | 1219219 A | | 1/1971 | | |
| WO | 2012/136133 A1 | | 10/2012 | | |
| WO | WO-2012136133 A1 | * | 10/2012 | ........... | A61K 31/568 |

OTHER PUBLICATIONS

Extended European Search Report corresponding to EP 15847156.5 dated Sep. 14, 2017, 11 pages.
Wang, W. C. et al., "Anordiol is More Potent than Anordrin for Terminating Pregnancy When Administered with RU 486," *Contraception* (accepted for Pub Apr. 9, 1993); 47:609-616.
International Search Report dated Jan. 8, 2016 for PCT/CN2015/090951 filed Sep. 28, 2015, 2 pages.

* cited by examiner

*Primary Examiner* — Daniel M Podgorski
(74) *Attorney, Agent, or Firm* — Mintz Levin Cohn Ferris Glovsky and Popeo PC (57) ABSTRACT

An oral formulation, and preparation method and use thereof; the oral formulation comprises 1-50 parts by weight of an A-nor-5a-androstane compound, 20-95 parts by weight of a filling agent, 0-20 parts by weight of a disintegrant, 0.1-30 parts by weight of a binder, 0.1-5 parts by weight of a lubricant and 0.1-5 parts by weight of a glidant. The oral formulation has a high stability and a good dissolution performance.

8 Claims, 2 Drawing Sheets

ORAL FORMULATION OF A-NOR-5α ANDROSTANE COMPOUND

TECHNICAL FIELD

The present invention relates to medical field, in particular, to an oral formulation of an A-nor-5α androstane compound having an anti-cancer effect and an anti-prostatic hyperplasia effect.

BACKGROUND

Active ingredient A-nor-5α androstane compound is a novel compound developed by Li Ruilin et al through independent researches in 2000. Animal efficacy tests showed a good effect on treating benign prostatic hyperplasia. A related invention patents is shown as patent No.: ZL00116781.2.

Later, upon a further long-term study, the inventor noticed the significant in-vivo and in-vitro anti-malignant tumor activity of the products, and it can be designed for preparing anti-malignant tumor medications (Application No.: 201110088946.4). The new anti-tumor drug, A-nor-5α androstane compound, is a novel tumor angiogenesis inhibitor (TAI). TAI is different from traditional chemotherapeutic drugs in that it starves cancers through inhibiting or destroying tumor angiogenesis and cutting off the source of tumor nutrition. TAI drugs are highly selective. They kill local cancer cells and systemic metastases with low toxicity to normal cells. The efficacy test shows that, A-nor-5α androstane compounds have a significant inhibition on cancer growth, inhibition on cancer proliferation and an advantage of improvement of animal weight reduction. It can selectively inhibit the division of the tumor cells without affecting the normal cells, thereby inhibiting the spread of tumor cells, and is a novel anti-tumor drug with good efficacy and low toxicity.

Currently, there is no preparation for A-nor-5α androstane compounds and no study has been reported. Therefore, there is a need in the art for providing an effective, stable and controllable dosage form which facilitates its therapeutic effect.

SUMMARY OF THE INVENTION

The object of the present invention is to provide a novel oral formulation with A-nor-5α androstane compound as the active ingredient. It has a stable and controllable quality and can be well-absorbed, which facilitates the main drug to exhibit therapeutical effects In the first aspect of the present invention, an oral formulation is provided; comprising an A-nor-5α androstane compound as an active ingredient, and the oral formulation has one or more characteristics selected from a group consisting of:

(i) under pH 5.0-8.0, the dissolution rate $Y_{30}$ of A-nor-5α androstane compound in said formulation within 30 minutes is ≥80%, preferably $Y_{30}$≥85%, more preferably $Y_{30}$≥90%;

(ii) under pH 5.0-8.0, the dissolution rate $Y_{60}$ of A-nor-5α androstane compound in said formulation within 60 minutes is ≥80%, preferably $Y_{60}$≥85%, more preferably $Y_{60}$≥90%;

and said oral formulation further has one or more characteristics selected from the group consisting of:

(a) $X1$≥85%, wherein $X1=Y1/Y_{30}$; Y1 is a dissolution rate of the A-nor-5α-androstane compound in said oral formulation within 30 minutes under pH 5.0-8.0 after stored for 30 days at a temperature of 40° C.±2° C. and a relative humidity of 75%±5%; preferably $X1$≥90%, even $X1$≥95%;

(b) $X2$≥85%, wherein $X2=Y2/Y_{30}$; Y2 is a dissolution rate of the A-nor-5α-androstane compound in said oral formulation within 30 minutes under pH 5.0-8.0 after stored for 60 days at a temperature of 40° C.±2° C. and a relative humidity of 75%±5%; preferably $X2$≥90%, even $X2$≥95%;

(c) $X3$≥85%, wherein $X3=Y3/Y_{30}$; Y3 is a dissolution rate of the A-nor-5α-androstane compound in said oral formulation within 30 minutes under pH 5.0-8.0 after stored for 180 days at a temperature of 40° C.±2° C. and a relative humidity of 75%±5%; preferably $X3$≥90%;

(d) $X4$≥85%, wherein $X4=Y4/Y_{30}$; Y4 is a dissolution rate of the A-nor-5α-androstane compound in said oral formulation within 30 minutes under pH 5.0-8.0 after stored for 365 days at a temperature of 25° C.±2° C. and a relative humidity of 60%±10%; preferably $X4$≥90%;

(e) $X5$≥85%, wherein $X5=Y5/Y_{60}$; Y5 is a dissolution rate of the A-nor-5α-androstane compound in said oral formulation within 60 minutes under pH 5.0-8.0 after stored for 30 days at a temperature of 40° C.±2° C. and a relative humidity of 75%±5%; preferably $X5$≥90%;

(f) $X6$≥85%, wherein $X6=Y6/Y_{60}$; Y6 is a dissolution rate of the A-nor-5α-androstane compound in said oral formulation within 60 minutes under pH 5.0-8.0 after stored for 60 days at a temperature of 40° C.±2° C. and a relative humidity of 75%±5%; preferably $X6$≥90%;

(g) $X7$≥85%, wherein $X7=Y7/Y_{60}$; Y7 is a dissolution rate of the A-nor-5α-androstane compound in said oral formulation within 60 minutes under pH 5.0-8.0 after stored for 180 days at a temperature of 40° C.±2° C. and a relative humidity of 75%±5%; preferably $X7$≥90%;

(h) $X8$≥85%, wherein $X8=Y8/Y_{60}$; Y8 is a dissolution rate of the A-nor-5α-androstane compound in said oral formulation within 60 minutes under pH 5.0-8.0 after stored for 365 days at a temperature of 25° C.±2° C. and a relative humidity of 60%±10%; preferably $X8$≥90%.

In another preferred embodiment, the dissolution rate of A-nor-5α-androstane compound in said oral formulation within 30 minutes under pH 6.0 PBS is ≥90%.

In another preferred embodiment, after stored for 10 days at a high temperature of 60° C., a high humidity of 92.5% and an intensity of illumination of 4500 lx, the dissolution rate of A-nor-5α-androstane compound in said oral formulation within 30 minutes under pH 6.0 PBS is ≥85; preferably ≥90%.

In another preferred embodiment, after stored for 3 months, 6 months, and even 1 year, the dissolution rate of the A-depleted-5 alpha androstane compound of said oral formulation within 30 min under the condition of pH 6.0 PBS is up to 85%, and preferably, the dissolution rate is ≥90%.

In another preferred embodiment, said formulation comprises components of the following parts by weight:

|  | parts by weight | preferred parts by weight |
|---|---|---|
| active ingredient | 1-50 parts by weight | 1-25 parts by weight |
| filling agent | 20-95 parts by weight | 30-90 parts by weight |
| disintegrant | 0-20 parts by weight | 1-10 parts by weight |
| binder | 0.1-30 parts by weight | 0.5-10 parts by weight |
| lubricant | 0.1-5 parts by weight | 0.2-2.5 parts by weight |
| glidant | 0.1-5 parts by weight | 0.2-2.5 parts by weight | wherein, said active ingredient is an A-nor-5α-androstane compound.

In another preferred embodiment, most of components other than the active ingredient are water-soluble adjuvants, wherein the total weight of the water-insoluble adjuvants is 0-20% by weight of the adjuvant of said oral formulation, preferably 0-10%, most preferably 0-5%.

In another preferred embodiment, the weight of the above mentioned components is 70-100%, preferably 80-100%, more preferably 90-100%, most preferably 95-100%, based on the total weight of the oral formulation.

In another preferred embodiment, the content of microcrystalline cellulose in the oral formulation is ≤10 wt %, preferably ≤5 wt %, more preferably ≤1 wt %, and most preferably, the content of microcrystalline cellulose is 0 wt %.

In another preferred embodiment, said filling agent is one or more selected from the group consisting of lactose, sucrose, sorbitol, mannitol, polyethylene glycol, starch and inorganic salts; and/or said disintegrant is one or more selected from the group consisting of crospovidone (PVPP), croscarmellose sodium (CC Na), sodium carboxymethyl starch (CMS-Na), low-substituted hydroxypropylcellulose (L-HPC); and/or said lubricant is one or more selected from the group consisting of stearic acid, sodium stearate, magnesium stearate, calcium stearate, polyethylene glycol, and hydrogenated vegetable oil; and/or said binder is one or more selected from the group consisting of starch slurry, hydroxypropylmethylcellulose (HPMC), povidone (PVP) and copovidone (Kollidon); and/or said glidant is one or more selected from of the group consisting of aerosil and talcum powder.

In another preferred embodiment, said formulation is a tablet, granule, or capsule.

In the second aspect of the present invention, an oral formulation is provided, comprising components of the following parts by weight:

|  | parts by weight | preferred parts by weight |
| --- | --- | --- |
| active ingredient | 1-50 parts by weight | 1-25 parts by weight |
| filling agent | 20-95 parts by weight | 30-90 parts by weight |
| disintegrant | 0-20 parts by weight | 1-10 parts by weight |
| binder | 0.1-30 parts by weight | 0.5-10 parts by weight |
| lubricant | 0.1-5 parts by weight | 0.2-2.5 parts by weight |
| glidant | 0.1-5 parts by weight | 0.2-2.5 parts by weight | wherein, said active ingredient is an A-nor-5α-androstane compound.

In another preferred embodiment, in addition to the active ingredient, said formulation basically comprises water-soluble adjuvants.

In another preferred embodiment, the total weight of the water-insoluble adjuvants is 0-20% by weight of the adjuvant of said oral formulation, preferably 0-10%, most preferably 0-5%.

In another preferred embodiment, the weight of the above mentioned components is 70-100%, preferably 80-100%, more preferably 90-100%, most preferably 95-100%, based on the total weight of the oral formulation.

In another preferred embodiment, the content of microcrystalline cellulose in the oral formulation is ≤10 wt %, preferably ≤5 wt %, more preferably ≤1 wt %, and most preferably, the content of microcrystalline cellulose is 0 wt %.

In another preferred embodiment, said filling agent is one or more selected from the group consisting of lactose, sucrose, sorbitol, mannitol, polyethylene glycol, starch and inorganic salts; and/or said disintegrant is one or more selected from the group consisting of crospovidone (PVPP), croscarmellose sodium (CC Na), sodium carboxymethyl starch (CMS-Na), low-substituted hydroxypropylcellulose (L-HPC); and/or said lubricant is one or more selected from the group consisting of stearic acid, sodium stearate, magnesium stearate, calcium stearate, and polyethylene glycol; and/or said binder is one or more selected from the group consisting of starch slurry, hydroxypropylmethylcellulose (HPMC), povidone (PVP) and copovidone (Kollidon); and/or said glidant is one or more selected from of the group consisting of aerosil and talcum powder.

In another preferred embodiment, said formulation is a tablet, granule, or capsule.

In another preferred embodiment, the weight of the tablet is 110-130 mg or 230-250 mg.

In another preferred embodiment, the content of A-nor-5α-androstane compound in the tablet is 1-100 mg/tablet, preferably 1-50 mg/tablet.

In another preferred embodiment, the dissolution performance of the oral formulation is described as the first aspect.

In the third aspect of the present invention, a method for preparing the oral formulation according to the first or the second aspect of the present invention is provided, comprising the following steps:

(1) providing the following materials as raw material:

|  | parts by weight | preferred parts by weight |
| --- | --- | --- |
| active ingredient | 1-50 parts by weight | 1-25 parts by weight |
| filling agent | 20-95 parts by weight | 30-90 parts by weight |
| disintegrant | 0-20 parts by weight | 1-10 parts by weight |
| binder | 0.1-30 parts by weight | 0.5-10 parts by weight |
| lubricant | 0.1-5 parts by weight | 0.2-2.5 parts by weight |
| glidant | 0.1-5 parts by weight | 0.2-2.5 parts by weight | wherein, said active ingredient is an A-nor-5α-androstane compound.

(2) preparing said oral formulation from the above materials.

In another preferred embodiment, a method, such as direct powder compression, wet granulation or dry granulation is used for preparing oral formulation in step (2).

In another preferred embodiment, said formulation is prepared by using direct powder compression, comprising the following steps:

a1) mixing the active ingredient, filing agent, disintegrant and binder by using equal increment method;

b1) adding lubricant and glidant into the mixture obtained in step a1), and homogenously mixing and tabletting the mixture to obtain said formulation.

In another preferred embodiment, said formulation is prepared by using wet granulation, comprising the following steps:

a2) homogenously mixing the active ingredient, filing agent, and disintegrant by using equal increment method;

b2) adding binder into the mixture obtained in step a2) to produce a soft material c2) granulating and pelletizing the soft material obtained in step b2) and adding disintegrant, lubricant and glidant as desired to produce said formulation.

In another preferred embodiment, said formulation is prepared by using dry granulation, comprising the following steps:

a3) homogenously mixing the active ingredient, filing agent, disintegrant, binder and glidant by using equal increment method;

b3) dry-granulating the mixture obtained in step a3), adding lubricant and disintegrant, homogenously mixing the product, and tabletting it to obtain said formulation.

According to the present invention, the structure of said A-nor-5α-androstane compound is shown in Formula I:

wherein, $R^1$, $R^2$ is independently selected from the group consisting of H, substituted or unsubstituted $C_{1-10}$ alkyl, substituted or unsubstituted $C_{3-8}$ cycloalkyl, substituted or unsubstituted benzene ring, substituted or unsubstituted benzoyl, substituted or unsubstituted —$COC_nH_{2n+1}$, substituted or unsubstituted —$COC_rH_{2r}COOC_mH_{2m++1}$, and —$COC_pH_{2p}COO^-W$; wherein each of n, p, r and m is independently an integer of 0 to 18, W is $H^+$, $Na^+$, $K^+$, $NH_4^+$, $½Ca^{2+}$, $½Mg^{2+}$, $½(AlOH)^{2+}$, or $½Zn^{2+}$, and the term "substituted" refers to one or more (e.g. 1-3) substituents selected from the group consisting of: hydroxyl, halogen, nitro, amino, amido, and carboxy.

Preferably, said A-nor-5α-androstane compound is:
2α, 17α-diethynyl-A-nor-5α-androstane-2β, 17β-dihydroxy compound;
2α, 17α-diethynyl-A-nor-5α-androstane-2β, 17β-dihydroxy diacetate compound;
2α, 17α-diethynyl-A-nor-5α-androstane-2β, 17β-dihydroxydipropionate compound;
2α, 17α-diethynyl-A-nor-5α-androstane-2β, 17β-dihydroxy-2β-mono succinate compound (Id)
2α, 17α-diethynyl-A-nor-5α-androstane-2β, 17β-disuccinate compound;
2α, 17α-diethynyl-A-nor-5α-androstane-2β, 17β-dibutyrate compound;
2α, 17α-dihydroxypropynyl-A-nor-5α-androstane-2β, 17β-dihydroxy compound;
2α, 17α-dicyano-A-nor-5α-androstane-2β, 17β-dihydroxy compound;
2α, 17α-diethynyl-A-nor-5α-androstane-2β, 17β-dihydroxy-di-(trichloroacetate) compound;
2α, 17α-diethynyl-A-nor-5α-androstane-2β, 17β-dihydroxy-2β-propionate-17β succinate compound;
2α, 17α-dipropynyl-A-nor-5α-androstane-2β, 17β-dihydroxy compound; or
2α, 17α-dipropynyl-A-nor-5α-androstane-2β, 17β-dihydroxy bipropionate compound.

In the forth aspect of the present invention, a use of the oral formulation according to the first or the second aspect is to provide for (i) preparing an anti-cancer medicament; or (ii) preparing a medicament for treating prostate hyperplasia.

In another preferred embodiment, said formulation is used for treating cancer or prostate hyperplasia and the dosage is 2.5-20 mg/each time, 1-4 times per day for administration.

In another preferred embodiment, said cancer is prostate cancer, liver cancer, pancreatic cancer, gastric cancer, intestinal cancer, or lung cancer.

In the oral formulation of the present invention, the active ingredient of has a remarkable inhibitory effect on the growth of malignant tumor cells and it is a novel anti-malignant tumor drug with low toxicity, good therapeutic effect and targeting effect. Such compounds specifically act on tumor cells, without affecting normal cells. The active ingredient also has an effect on anti-prostatic hyperplasia. There is good compatibility between the active ingredient and the adjuvant in the oral formulation of the present invention, and the oral formulation possesses high stability, convenient administration and better dissolution performance. For example, the dissolution rate of said oral formulation after stored at a temperature of 40° C.±2° C. and a relative humidity of 75%±5% or a temperature of 25° C.±2° C. and a relative humidity of 60%±10% for 30-365 days is ≥85%, or even ≥90% or ≥95%, compared with the dissolution rate before storage. It represents a stable and controllable quality, as well as a safe and reliable use, and thus great social and economic benefits.

It is to be understood that within the scope of the present invention, the above-described technical features of the present invention and the technical features specifically described in the following (e.g., examples) may be combined with each other to form a new or preferred technical solution. Limited to space, no longer in this one tired.

DETAILED EMBODIMENT

Upon an intensive and extensive study, the inventors of the present invention surprisingly developed an oral formulation with A-nor-5α-androstane compound as active ingredient and various adjuvant, wherein the amount of the water-insoluble adjuvant is less than 20% by the total weight of the adjuvants of said oral formulation, the content of microcrystalline cellulose is ≤10 wt %, preferably ≤5 wt %, more preferably ≤1 wt %, and the most preferably, the content of microcrystalline cellulose in said oral formulation is 0. Under pH 6.0 PBS, the dissolution rate of A-nor-5α-androstane compound in said formulation within 30 minutes is ≥80%, preferably ≥90%, more preferably ≥90%. The ratio of the dissolution rate of A-nor-5α-androstane compound in said formulation under pH 5.0-8.0 within 30 mins or 60 mins after stored for 30, 60, 120, 365 days to that before storage is ≥85%, preferably ≥90%, even ≥95%. The quality of oral formulation of the present invention is stable and controllable; it can be well dissolved and absorbed in the digestive tract and facilitate the active ingredient to exert its effects. The present invention is accomplished on this basis.

Active Ingredient

According to the present invention, the term "active ingredient" refers to A-nor-5α-androstane compound with the following structure:

(I)

wherein, $R^1$, $R^2$ is independently selected from the group consisting of H, substituted or unsubstituted $C_{1-10}$ alkyl, substituted or unsubstituted $C_{3-8}$ cycloalkyl, substituted or unsubstituted benzene ring, substituted or unsubstituted benzoyl, substituted or unsubstituted —$COC_nH_{2n+1}$, substituted or unsubstituted —$COC_rH_{2r}COOC_mH_{2m++1}$, or —$COC_pH_{2p}COO^-W$; wherein n, p, r and m are each independently an integer of 0 to 18, W is $H^+$, $Na^+$, $K^+$, $NH_4^+$, $½Ca^{2+}$, $½Mg^{2+}$, $½(AlOH)^{2+}$, or $½Zn^{2+}$.

and the term "substituted" refers to one or more (e.g. 1-3) substituents selected from the group consisting of: hydroxyl, halogen, nitro, amino, amido, and carboxy.

Preferably, said A-nor-5α-androstane compound is:

2α, 17α-diethynyl-A-nor-5α-androstane-2β, 17β-dihydroxy compound (Ia);

2α, 17α-diethynyl-A-nor-5α-androstane-2β, 17β-dihydroxy diacetate compound (Ib);

2α, 17α-diethynyl-A-nor-5α-androstane-2β, 17β-dihydroxydipropionate compound (Ic);

2α, 17α-diethynyl-A-nor-5α-androstane-2β, 17β-dihydroxy-2β-mono succinate compound (Id)

2α, 17α-diethynyl-A-nor-5α-androstane-2β, 17β-disuccinate compound (Ie);

2α, 17α-diethynyl-A-nor-5α-androstane-2η, 17β-dibutyrate compound (If);

2α, 17α-dihydroxypropynyl-A-nor-5α-androstane-2β, 17β-dihydroxy compound (Ig);

2α, 17α-dicyano-A-nor-5α-androstane-2β, 17β-dihydroxy compound (Ih);

2α, 17α-diethynyl-A-nor-5α-androstane-2β, 17β-dihydroxy-di-(trichloroacetate) compound (Ii)

2α, 17α-diethynyl-A-nor-5α-androstane-2β, 17β-dihydroxy-2β-propionate-17β succinate compound (Ij);

2α, 17α-dipropynyl-A-nor-5α-androstane-2β, 17β-dihydroxy compound (Ik); or

2α, 17α-dipropynyl-A-nor-5α-androstane-2β, 17β-dihydroxy bipropionate compound (Il).

Oral Formulation

The present invention relates to an oral formulation by using A-nor-5α-androstane compound as active ingredient and provides the basis for study on pharmaceutical preparation with pre-recipe research.

The results of the pre-prescription research indicated that: the water-insoluble medicament, A-nor-5α-androstane compound (it is classified as water insoluble according to the pharmacopeia since the water dissolution rate is 6.5 μg/ml), can be well-dissolved and absorbed in intestinal liquid. It mainly relies on passive diffusion mechanism for transport, uptake and absorb in the body and the uptake amounts are dependent on the time and dose. A-nor-5α-androstane compound can be administered by oral pathway. The patient compliance can be enhanced since long-term administration is necessary for the cancer therapy and the oral formulation can be easy-administered. Therefore, an oral formulation, such as ordinary oral tablet, oral capsule and other sustained-release preparation, is designed according to the present invention.

The components and the parts by weight thereof in the oral formulation of the present invention are shown as followed:

| components of the recipe | Parts by weight |
| --- | --- |
| active ingredient | 1-50 |
| filling agent | 20-95 |
| disintegrant | 0-20 |
| binder | 0.1-30 |
| lubricant | 0.1-5 |
| glidant | 0.1-5 | wherein said active ingredient is an A-nor-5α-androstane compound;

the filling agent to be added can be one or more ingredients used for enhancing the weight and volume of the tablet. According to the present invention, said filling agent is one or more selected from the group consisting of lactose, sucrose, sorbitol, mannitol, polyethylene glycol, starch and inorganic salts. The amount of the filling agent is 20-95% by the total weight of the formulation, preferably 60-95%, more preferably 70-95%, the most preferably 80-95%. When lactose is used as a filling agent, the amount of lactose is 20-95% by the total weight of the formulation; when sucrose is used as a filling agent, the amount of sucrose is 10-30% by the total weight of the formulation; when sorbitol is used as a filling agent, the amount of sorbitol is 20-95% by the total weight of the formulation; when mannitol is used as a filling agent, the amount of mannitol is 20-95% by the total weight of the formulation; when inorganic salt is used as a filling agent, the amount of inorganic salt is 5-20% by the total weight of the formulation. In another preferred embodiment, said filling agent is lactose, mannitol, sorbitol, or a combination thereof; preferably said filling agent is the mixture of lactose and mannitol.

Said disintegrant is one or more selected from the group consisting of crospovidone (PVPP), croscarmellose sodium (CC Na), sodium carboxymethyl starch (CMS-Na), low-substituted hydroxypropylcellulose (L-HPC); wherein PVPP and CCNa are preferred with CCNa being the most preferred. The amount of disintegrant is 0-20% by the total weight of the formulation, generally 1-10%, the most preferably 3-5%.

Said lubricant is one or more selected from the group consisting of stearic acid, sodium stearate, magnesium stearate, calcium stearate, polyethylene glycol, hydrogenated vegetable oil; wherein the magnesium stearate is the most preferred. The amount of the lubricant is 0.1-5% by the total weight of the formulation, generally 0.2-4%, the most preferably 0.3-3%.

The binder can be one or more ingredients facilitating granulation. Said binder is one or more selected from the group consisting of starch slurry, hydroxypropylmethylcellulose (HPMC), polyethylene, povidone (PVP) and copovidone (Kollidon). PVP is preferred. When starch slurry is used as the binder, the amount of the starch slurry is 10-30% by the total weight of the formulation; when HPMC is used as a binder, the amount of HPMC is 2-5% by the total weight of the formulation; when PVP is used as a binder, the amount of PVP is 2-20% by the total weight of the formulation; when copovidone is used as a binder, the amount of the copovidone is 0.1-10% by the total weight of the formulation Said glidant is one or more selected from of the group consisting of aerosil and talcum powder; wherein the aerosil is preferred.

In another preferred embodiment, said inorganic salt is selected from: calcium sulfate comprising two molecules of crystal water; calcium hydrphosphate, officinal calcium carbonate, etc.

Generally, the tablet of the present invention may contain any other adjuvant which is obvious for those skilled in the art. The tablet of the present invention can be prepared by preparation methods well-known to those skilled in the art. For example, a method such as direct powder compression, wet granulation or dry granulation is used for preparing tablet.

The present invention provides a tablet comprising A-nor-5α androstane compound, clinical dose of which is determined based on a pharmacological study. To meet the clinical need, the dose of A-nor-5α androstane compound tablets is determined as 1-100 mg/tablet, preferably 1-50 mg/tablet, such as 2.5 mg/tablet, 5 mg/tablet, 10 mg/tablet, or 25 mg/tablet.

The features mentioned above, or the features mentioned in the embodiments, may be combined in any forms. All features disclosed in this specification may be used in conjunction with any form of the composition, and each feature disclosed in the specification may be substituted by any alternative feature that provides the same, equal or similar purpose. Thus, unless otherwise specified, the features disclosed are only general examples of equal or similar features.

The advantages of the present invention are:

(1) A novel oral formulation comprising A-nor-5α androstane compound as active ingredient is provided. It can be well-dissolved and absorbed in the intestinal tract and it fills the gap in the dosage form of A-nor-5α androstane compound.

(2) The recipe of the oral formulation according to the present invention is simple and reasonable. Water-soluble filling agents are mainly instead of conventional water-insoluble filling agent such as microcrystalline cellulose. The oral formulation is of stable and controllable quality, which facilitates the active ingredient to exert its therapeutic effects.

(3) The preparation process of the oral formulation according to the present invention is easy to conduct and it can be ready for industrial production.

(4) The oral formulation according to the present invention has a nice appearance, is convenient for administration, save and reliable, easily acceptable for the patient and has a high social and economic value.

The invention will now be further described with reference to specific embodiments. It is to be understood that these examples are merely illustrative of the invention and are not intended to limit the scope of the invention. The experimental methods not specified in the following examples are generally prescribed in accordance with conventional conditions or in accordance with the conditions recommended by the manufacturer. Unless otherwise stated, the percentages and parts are percentages by weight and parts by weight.

Unless otherwise defined, all professional and scientific terms used herein are of the same meaning as those skilled in the art are familiar with. In addition, any method and material similar to or equivalent to the contents described may be applied to the method of the present invention. The preferred embodiments and materials described herein are for exemplary purposes only.

General Methods

Dissolution Rate

According to the second paddle method described in <Determination Method for Dissolution Rate> (Appendix XC, Chinese Pharmacopoeia, 2010), the tests for dissolution rate were conducted. The instrument and device were adjusted before the test to ensure a distance of 25 mm±2 mm between bottom of the paddle and the inner bottom of the beaker and the rotate speed was set as 50 rpm. Dissolving medium upon degassing process, such as 900 ml of phosphate buffer (pH 6.0) was respectively measured and added into each dissolving beaker. The temperature of the dissolving medium was kept at 37° C.±0.5° C., and then 6 pieces of samples were respectively taken and placed into 6 dissolving beakers. Note that bubbles on the sample surface should be avoided. The instrument was turn on and timing was started; and at the specified sampling time (5, 10, 15, 30, 45, 60 min), 10 mL of the dissolved liquid was taken and immediately filtered through millipore filter membrane, and it should be completed within 30 seconds from sampling to filtration. The clear filtrate was subjected to HPLC tests to calculate the dissolving amount of each tablet.

Further, according to <Guidelines for Stabilization Tests of Crude Drugs and Pharmaceutic Preparations> (Appendix XIXC, Chinese Pharmacopoeia, 2010), the tablets comprising A-nor-5α androstane compound were subject to accelerating tests and long-term tests under conditions of high temperature (60° C.), high humidity (25° C., relative humidity 92.5%), and high-light exposure (4500 lx) to determine the dissolution rates of the samples and the obtained results were compared with those of the sample on day 0.

Example 1

Confirmation of Administration Route

The administration route of the formulation comprising A-nor-5α androstane compound should be confirmed since it is a novel medicament of Category I. In the present example, the pre-recipe works, such as solubility, oil-water partition coefficients, cell transport, cell uptake and gastric absorption, etc. of the A-nor-5α androstane compounds was studied so as to provide the basis for confirming the administration route.

1.1 Determination on Equilibrium Solubility

Phosphate buffer solution (PBS) with different pH was prepared (pH is 1.0, 5.0, 5.5, 5.8, 6.0, 6.8 and 7.4). The equilibrium solubility of A-nor-5α androstane compounds (Ia) in PBS with different pH was determined by using Equilibrium Method. Method: 5 mL of each medium was removed into test tubes with plug and about 30 mg of crude drugs comprising A-nor-5α androstane compounds were added into the tubes respectively. The tubes were subjected to a thermostatic oscillator (37° C.) and vibrated at 100 rpm. After 72 hours, the sample was taken and subjected to HPLC analysis. The results are shown in Table 1.

TABLE 1

Equilibrium solubility of A-nor-5 α androstane
compounds (Ia) in different mediums (n = 3).

| medium | equilibrium solubility (µg/mL) | medium | equilibrium solubility (µg/mL) |
|---|---|---|---|
| — | — | pH 5.8 PBS | 70.52 ± 1.28 |
| pH 1.0 hydrochloric acid | 7.85 ± 0.57 | pH 6.0 PBS | 144.54 ± 0.77 |
| pH 5.0 PBS | 14.73 ± 0.80 | pH 6.8 PBS | 1388.16 ± 90.95 |
| pH 5.5 PBS | 45.73 ± 0.23 | pH 7.4 PBS | 4507.97 ± 487.04 |

The results show that the solubility of A-nor-5α androstane compound is dependent on pH and it rises with the increase in pH of PBS. Due to the relationship between dissolution and solubility, A-nor-5α androstane compound rarely dissolves under an acidic condition. Accordingly, the dissolution of the drug may be a rate-limiting step of the absorption. Under the jejunum and ileum pH conditions (the pH value in the jejunum is 6.5, the pH of the proximal small intestine is 7, the pH in the distal ileum is 7.5), the solubility of the A-nor-5α androstane compound was large, and dissolution may not be a key factor affecting the absorption of A-nor-5-androstane compound.

1.2 Oil-Water Partition Coefficient

PBS with different pH was prepared, and oil-water partition coefficient of A-nor-5α androstane compound (Ia) in a buffer solution with different pH (e.g., 2.0, 4.5, 5.0, 6.0, 6.8, 7.4, respectively) was determined by shake-flask method. Water-saturated n-octanol was used to prepare a stock solution of A-nor-5α androstane compound, concentration of which was about 10 mg/mL. A variety of n-octanol-saturated PBS and aqueous solution (5 ml) was taken and added into glass tubes with plug. 0.5 mL of stock solution of A-nor-5α-androstane compound was added. The tubes were sealed completely and subjected to a 37° C. thermostatic oscillator, and sampled after shaking for 24 h. Samples from water phase and oil phase were taken for analysis by HPLC, respectively. The drug concentrations in water and oil phase were calculated. According to Log P=–Log ($C_{oil}/_{water}$), oil-water partition coefficient (Log P) was calculated and the results are shown in Table 2.

TABLE 2

Determination of oil-water partition coefficient of A-nor-5α-androstane
compound in buffer solution with different pH (n = 3)

| pH | 2.0 | 4.5 | 5.0 | 6.0 | 6.8 | 7.4 |
|---|---|---|---|---|---|---|
| LogP | ∞ | 4.19 ± 0.084 | 3.80 ± 0.049 | 2.52 ± 0.006 | 0.98 ± 0.003 | 0.11 ± 0.0004 |

Generally, an excessively high drug Log P (>3) indicates that the lipid solubility of a drug is too high, so that the drug can not be released from the biological membrane; while an excessively low Log P (<–2) indicates that water solubility of a drug is too high, so that the drug can not readily penetrate the biological membrane as well as be absorbed; and the best Log P value of the drug is: –1<Log P<2.

The results showed that A-nor-5α-androstane compounds may be better absorbed under near-neutral conditions. While the pH values of different parts of the gastro-intestinal tract were: stomach 1.5-2.5, duodenal 5.5-6.1, jejunum 6.5, ileum 7, and colon 7.5. Therefore, A-nor-5α-androstane compounds may be better absorbed in the intestinal tracts.

1.3 Cell Tests In Vitro

Cell Transport

The qualified Transwell plate was taken. The nutrient solution comprising drugs was prepared by using Hank's balanced salt solution (HBSS) to study the bidirectional transfer of A-nor-5α-androstane compounds (Ia) with different concentrations in Caco-2 cells. The results are shown in Table 3.

TABLE 3

Results of cell transport tests of A-nor-5 α-androstane compounds (Ia)

| Concentration | $P_{app}$ (×10$^{-6}$ cm/s) | | |
|---|---|---|---|
| mg/mL | A-B | B-A | ER |
| 0.5 | 2.59 ± 0.17 | 5.02 ± 0.50 | 1.94 |
| 0.75 | 4.00 ± 0.15 | 6.46 ± 0.71 | 1.62 |
| 1.0 | 4.98 ± 0.16 | 9.07 ± 0.35 | 1.82 |

According to the results, the apparent permeability coefficient ($P_{app}$) of A-nor-5α-androstane compound in Caco-2 cells enhanced with the increase of concentration, but the efflux rate (ER) changed little. It was speculated that the major transport mechanism of A-nor-5α-androstane compound was passive diffusion. All $P_{apps}$ under various conditions are >1×10$^{-6}$ cm/s, suggesting that A-nor-5α androstane compound could be better absorbed in digestive tract.

Cells Uptake

Caco-2 cells were spotted on a six-well plate. When the cells were grown to an inoculation density of 8×10$^4$ cells/mL, the cells were cultured with the drug-containing medium. The relationship between cells uptake and uptake time, the concentration of A-nor-5α-androstane compound (Ia) were examined. After the experiment was completed, the cells were scraped off and the cells were broken by multiple freezing-thawing. The samples of the cells were precipitated by acetonitrile and then subjected to HPLC analysis.

According to the uptake tests, the uptake amounts exhibited linear relationship with the uptake time (Y=0.204x+6.107, r=0.9952) and the uptake amounts enhanced with the increase of the uptake time; the uptake amounts exhibited linear relationship with the concentration of the A-nor-5α-androstane compounds (Ia) (y=40.59x–10.47, r=0.9994) and the uptake amounts enhanced with the increase of the concentration of A-nor-5α-androstane compounds, suggesting that the uptake mechanism of A-loss-5α-androstane compounds is passive diffusion.

1.4 Rat Tests In Vivo

Intestinal Absorption In Vivo

A suitable concentration of intestinal circulating liquid comprising A-nor-5α-androstane compounds (Ia) was prepared by using PBS (pH 5.5 and pH 6.8) containing phenol red. Rats were fasting over 12 hours before the experiment and then subjected to intraperitoneal injection with urethane solution (dose 4 mL/kg) at a concentration of 0.3 g/ml for anesthesia. The rats were fixed and a 3 cm incision was made along the medioventral line. The duodenum (start from 1 cm below the pyloru, intestinal circulating fluid comprising A-nor-5α androstane compound, pH 5.5), the jejunum (start from 1 cm below the pylorus, intestinal circulating fluid comprising A-nor-5α androstane compound, pH 6.8), and the ileum (start from 30 cm below the pylorus, intestinal circulating fluid comprising A-nor-5α androstane compound, pH 6.8) were incubated and ligated. Preheated saline (37° C.) was used to clean the intestinal contents, and then the air (37° C.) was ventilated into the intestine to remove the saline. The wound was covered with dressing, and infrared lamp was used to keep warm (37° C.). The reflux device was connected and after 50 ml of drug-containing circulating fluid at a constant temperature of 37° C. was balanced at 3 mL/min for 5 min, timing was started when the flow rate was adjusted to 1 mL/ml. Samples (1 mL for each) were taken at 0, 15, 30, 45, 60, 90, and 120 min, while adding blank circulating fluid (1 mL). The sample was subjected to HPLC analysis after appropriate treatment. The volume of circulating fluid was corrected according to the concentration of phenol red. Then the remained amounts of drug X were calculated by the concentration of A-nor-5α androstane compounds and the volume of circulating fluid. Line slope is the absorption rate constant (Ka) of a drug. The cumulative absorption percentage (P) of the drug is obtained by comparing the absorption dose (Q) of a drug in 2 hours to the initial dose (X0) before absorption. The results are shown in Table 4 and Table 5.

TABLE 4

Absorption of A-nor-5 α androstane compounds (Ia) in different intestinal segment (n = 3)

| Intestinal segment | Q (μg/2 h) | P (%) | Ka ($\times 10^{-3}$ min) |
|---|---|---|---|
| Duodenum | 324.42 ± 65.21 | 45.48 ± 9.33 | 4.27 ± 1.53 |
| jejunum | 1809.26 ± 369.52 | 71.68 ± 13.48 | 9.53 ± 4.22 |
| ileum | 1603.03 ± 289.37 | 65.23 ± 11.80 | 7.57 ± 2.56 |

TABLE 5

Absorption of A-nor-5 α androstane compound (Ia) with different concentration in jejunum (n = 3)

| The concentration of A-nor-5 α androstane compound μg/mL | Q (μg/2 h) | P (%) | Ka ($\times 10^{-3}$ min) |
|---|---|---|---|
| 25.0 | 1063.39 ± 75.81 | 90.27 ± 3.28 | 18.87 ± 2.94 |
| 50.0 | 1809.26 ± 369.52 | 71.68 ± 13.48 | 9.53 ± 4.22 |
| 100.0 | 2636.52 ± 137.86 | 53.25 ± 2.77 | 5.50 ± 0.36 |

The results showed that A-nor-5α androstane compound can be better absorbed in jejunum and ileum. Both of the absorption percentages are lager than 50%. It was subjected to linear regression analysis based on lnX. All the r values of each regression line is larger than 0.9, indicating that the decrease in drug concentration exhibited a linear relationship with the cycle time in jejunum and ileum, suggesting the absorption kinetics of A-nor-5α androstane compound are primary absorption. There was a good linear relationship between the absorption of A-nor-5α-androstane compounds and concentration (y=20.34x+649.7, r=0.9869), indicating that the absorption mechanism of A-nor-5α-androstane compounds may be passive diffusion. The results of intestinal absorption showed that A-nor-5α-androstane compounds could be better absorbed in the small intestine.

1.5 Pharmacokinetic Study on Bioavailability

The product can be well absorbed in animal. Beagle dogs were administered with a drug at the dose of 1.0 mg/kg by gastric gavage, and based on the $AUC_{0-t}$ of crude drug, A-nor-5α androstane compound (Ia), the absolute bioavailability of the drug was 56.8%, and the absolute bioavailability is 93.0% based on the $AUC_{0-t}$ of total main metabolites in vivo.

Note: total main metabolites in vivo refer to the main metabolites and the crude drugs (A-nor-5α-androstane compounds) which were not metabolized and hydrolysates thereof.

The above pre-recipe studies indicated that A-nor-5α-androstane compounds could be well dissolved and absorbed in intestinal liquid and it can be administered via oral pathway. Further, patient compliance can be enhanced since the long-term administration is necessary for the cancer therapy and the oral formulation can be easy-administered. Accordingly, an oral formulation, such as ordinary oral tablet, oral capsule and other sustained-release preparation, is designed according to the present invention.

The components and the preparation of the oral formulation according to the present invention can be illustrated with reference to the following tablets as examples.

Example 2

| Tablet and the preparation thereof | |
|---|---|
| Components | Content (g)/1000 tablets |
| A-nor-5 α-androstane compound (Ia) | 50 |
| Lactose | 828 |
| Xylitol | 120 |
| Mannitol | 120 |
| crospovidone | 36 |
| HPMC | 36 |
| magnesium stearate | 6 |
| aerosil | 4 |

A-nor-5α-androstane compound (Ia) was homogenously mixed with xylitol, mannitol and lactose. The product was granulated with 12% (wt/v) aqueous solution of HPMC, dried at 40° C. and pelletized with 20-mesh sieve. The crospovidone, magnesium stearate and aerosil were added to the dry granules, and the product was homogenously mixed, and tableted for use.

Figure 1:
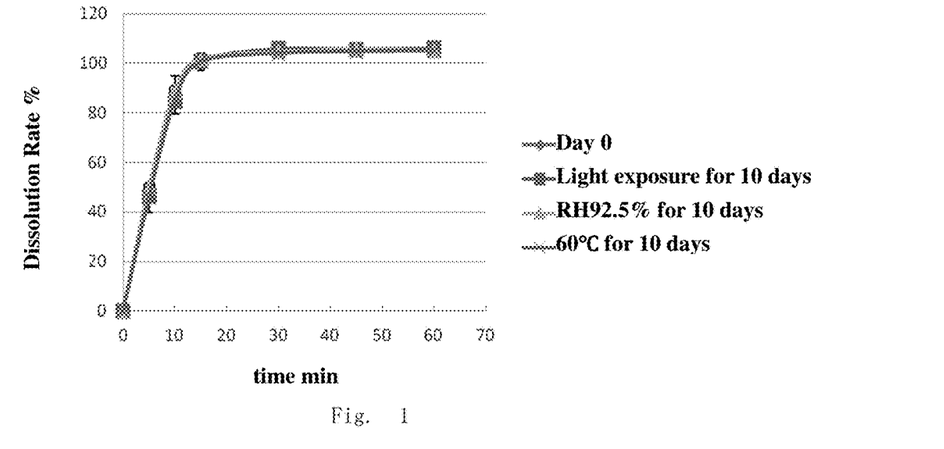
FIG. 1 is the dissolution profile of the tablets prepared in Example 2 under various conditions.

FIG. 1 shows the dissolving profiles of the sample on Day 0 and the samples stored for 10 days under various testing conditions of influence factors. The results showed that, under such dissolution conditions, the tablets comprising A-nor-5α-androstane compound could be completely dissolved within 30 mins (the dissolution rate is greater than or equal to 95%).

In addition, after stored under a condition of a relative humidity of 92.5% and a temperature of 25° C., a condition of light intensity of 4500 lx and a condition of a high temperature of 60° C. for 10 days, the tested ratio of A-nor-5α-androstane compound to other adjuvant was substantially in accordance with the ratio of those before storage, indicating that A-nor-5α-androstane compounds possess good compatibility with each adjuvant.

Example 3

| Tablets and the preparation thereof | |
|---|---|
| Components | Content (g)/ 1000 tablets |
| A-nor-5 α-androstane compound (Ib) | 20 |
| lactose | 1140 |

| Tablets and the preparation thereof | |
|---|---|
| Components | Content (g)/ 1000 tablets |
| crospovidone | 12 |
| copovidone K30 | 10 |
| magnesium stearate | 12 |
| talcum powder | 6 |

The A-nor-5α-androstane compound (Ib) was homogenously mixed with lactose and half of the amount of crospovidone in the recipe. The product was granulated with 4% (wt/v) aqueous solution of copovidone K30, dried at 40° C. and pelletized with 20-mesh sieve. The magnesium stearate, talcum powder and the rest amount of the crospovidone in the recipe was added into the dry granules. The product was homogenously mixed and tableted for use.

As tested, the dissolution rates within 30 mins of the sample on Day 0 and the samples stored under a condition of a high temperature of 60° C., light intensity of 4500 lx, and a high humidity of 92.5% for 10 days are larger than or equal to 95%.

Example 4

| Tablets and the preparation thereof | |
|---|---|
| Components | Content (g)/ 1000 tablets |
| A-nor-5 α-androstane compound (Id) | 600 |
| lactose | 210 |
| mannitol | 210 |
| copovidone K30 | 60 |
| magnesium stearate | 60 |
| aerosil | 60 |

The A-nor-5α-androstane compound (Id) was homogenously mixed with lactose and mannitol. The product was granulated with 20% (wt/v) povidone in aqueous ethanol (the volume ratio of ethanol to water is 3:7), dried at 40° C. and pelletized with 20-mesh sieve. The magnesium stearate and aerosil was added to the dry granules, and the product was homogenously mixed, and tableted for use.

As tested, the dissolution rates within 30 mins of the sample on Day 0 and the samples stored under a condition of a high temperature of 60° C., light intensity of 4500 lx, and a high humidity of 92.5% for 10 days are larger than or equal to 95%.

Example 5

| Tablets and the preparation thereof | |
|---|---|
| Components of a tablet | Content (g)/ 1000 tablets |
| A-nor-5 α-androstane compound (Ic) | 72 |
| mannitol | 600 |
| lactose | 390.6 |
| starch | 75 |
| CC Na | 60 |
| magnesium stearate | 1.2 |
| talcum powder | 1.2 |

The A-nor-5α-androstane compound (Ic) was homogenously mixed with mannitol, lactose and CC Na. The product was granulated with 25% (wt/v) starch slurry, half-dried at 40° C., pelletized with 20-mesh sieve, and dried. The magnesium stearate and talcum powder was added to the dry granules, and the product was homogenously mixed, and tableted for use.

Figure 2:
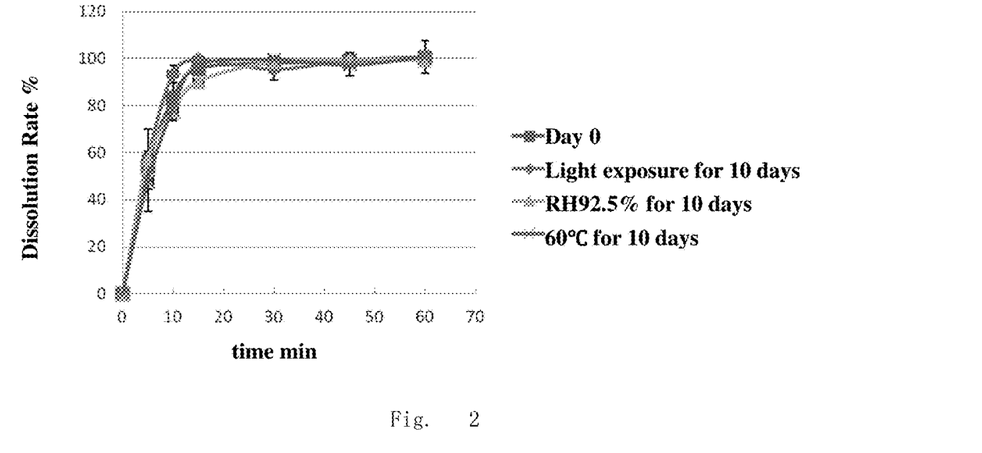
FIG. 2 is the dissolution profile of the tablets prepared in Example 5 under various conditions.

FIG. 2 shows the dissolving profiles of the sample on Day 0 and the samples stored for 10 days under various testing conditions of influence factors. The results showed that, under such dissolution conditions, the tablets comprising A-nor-5α-androstane compound could be completely dissolved within 30 mins (the dissolution rate is greater than or equal to 95%).

After stored under a condition of a relative humidity of 92.5% and a temperature of 25° C., a condition of light intensity of 4500 lx and a condition of a high temperature of 60° C. for 10 days, the tested ratio of A-nor-5α-androstane compound to other adjuvant was substantially in accordance with the ratio of those before storage, indicating that A-nor-5α-androstane compounds possess good compatibility with each adjuvant.

Example 6

| Tablets and the preparation thereof | |
|---|---|
| Components of the tablet | Content (g)/1000 tablets |
| A-nor-5α-androstane compound (Ie) | 48 |
| pregelatinized starch | 120 |
| calcium sulfate | 120 |
| sorbitol | 480 |
| CMS-Na | 240 |
| copovidone VA64 | 120 |
| polyethylene glycol | 36 |
| talcum powder | 36 |

The A-nor-5a-androstane compound (Ie) was homogenously mixed with sorbitol, pregelatinized starch, calcium sulfate and copovidone VA64. The product was dry-pressed and pelletized with 20-mesh sieve. The CMS-Na, polyethylene glycol and talcum powder was added to the dry granules, and the product was homogenously mixed, and tableted for use.

As tested, the dissolution rates within 30 mins of the sample on Day 0 and the samples stored under various testing conditions for 10 days are larger than or equal to 95%.

Example 7

| Tablets and the preparation thereof | |
|---|---|
| Components of the tablet | Content (g)/1000 tablets |
| A-nor-5α-androstane compound (If) | 120 |
| lactose | 720 |
| mannitol | 240 |
| HPMC | 42 |
| CC Na | 75.6 |
| aerosil | 1.2 |
| magnesium stearate | 1.2 |

The A-nor-5a-androstane compound (If) was homogenously mixed with HPMC, mannitol and lactose by using Equilibrium Method. The mixture was granulated with dry granulation. HPMC, aerosil and magnesium stearate were added to the granules and tableted.

Figure 3:
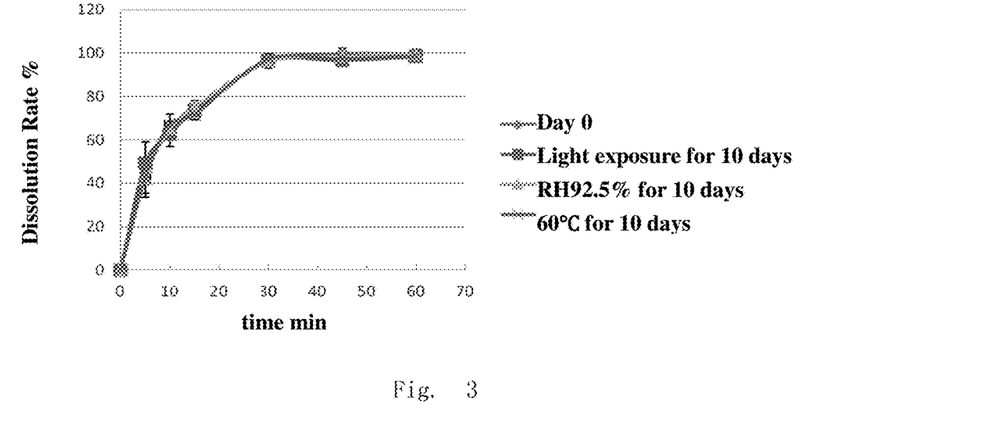
FIG. 3 is the dissolution profile of the tablets prepared in Example 7 under various conditions.

FIG. 3 shows the dissolving profiles of the sample on Day 0 and the samples stored for 10 days under a condition of influence factors (60° C., RH 92.5%, light exposure). The results showed that the tablets comprising A-nor-5α-androstane compound could be completely dissolved within 30 mins under such dissolution condition (the dissolution rate is greater than or equal to 95%).

Example 8

| Tablets and the preparation thereof | |
|---|---|
| Components of the tablet | Content (g)/1000 tablets |
| A-nor-5α-androstane compound (Ig) | 48.8 |
| pregelatinized starch | 720 |
| mannitol | 360 |
| copovidone VA64 | 1.2 |
| L-HPC | 36 |
| aerosil | 18 |
| magnesium stearate | 16 |

The A-nor-5a-androstane compound (Ig) was homogenously mixed with L-HPC, mannitol, pregelatinized starch and copovidone VA64, L-HPC, aerosil and magnesium stearate by using Equilibrium Method to homogenous. The obtained powder was directly tableted for use.

As tested, the dissolution rates within 30 mins of the sample on Day 0 and the samples stored under various testing conditions of influence factors for 10 days are larger than or equal to 95%.

Example 9

| Tablets and the preparation thereof | |
|---|---|
| Components of the tablet | Content (g)/1000 tablets |
| A-nor-5α-androstane compound (Ih) | 12 |
| lactose | 660 |
| mannitol | 258 |
| sodium carboxymethylcellulose | 120 |

| Tablets and the preparation thereof | |
|---|---|
| Components of the tablet | Content (g)/1000 tablets |
| copovidone VA64 | 120 |
| magnesium stearate | 18 |
| talcum powder | 12 |

The A-nor-5a-androstane compound (Ih) was homogenously mixed with copovidone VA64, mannitol, lactose and sodium carboxymethylcellulose by using Equilibrium Method. The magnesium stearate and talcum powder was added into the above mixture and homogenously mixed by using Equilibrium Method. The obtained powder was directly tableted for use.

Figure 4:
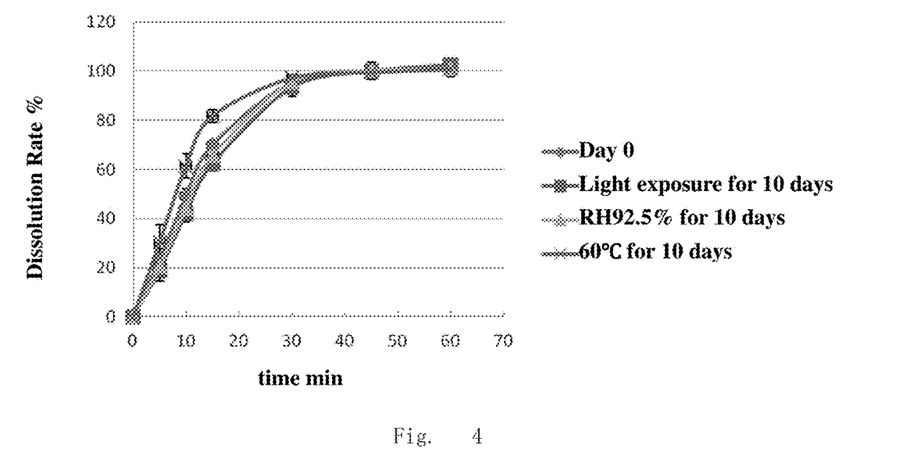
FIG. 4 is a dissolution profile of the tablets prepared in Example 9 under various conditions.

FIG. 4 shows the dissolving profiles of the sample on Day 0 and the samples stored for 10 days under a condition of influence factors (60° C., RH 92.5%, light exposure). The results showed that the tablets comprising A-nor-5α-androstane compound could be completely dissolved within 30 mins under such dissolution condition (the dissolution rate is greater than or equal to 95%).

Example 10

| Tablets and the preparation thereof | |
|---|---|
| Components of the tablet | Content (g)/1000 tablets |
| A-nor-5α-androstane compound (Ii) | 66 |
| mannitol | 480 |
| pregelatinized starch | 240 |
| copovidone VA64 | 120 |
| crospovidone | 240 |
| magnesium stearate | 36 |
| aerosil | 18 |

The process was essentially identical with that of Example 5 except that the ingredients of the tablet were different which are shown as above.

As tested, the dissolution rates within 30 min of the sample on Day 0 and the samples stored under various testing conditions of influence factors for 10 days are larger than or equal to 95%.

Example 11

| Tablets and the preparation thereof | |
|---|---|
| Components of the tablet | Content (g)/1000 tablets |
| A-nor-5α-androstane compound (Ii) | 66 |
| mannitol | 480 |
| pregelatinized starch | 240 |
| copovidone VA64 | 120 |
| crospovidone | 240 |
| magnesium stearate | 36 |
| aerosil | 18 |

The process was essentially identical with that of Example 5 except that the ingredients of the tablet were different which are shown as above and 2α, 17α-diethynyl-A-nor-5α-androstane-2β, 17β-dihydroxy-2β-propionate-17β succinate compound (Ij), 2α, 17α-dipropynyl-A-nor-5α-androstane-2β, 17β-dihydroxy compound (Ik), and 2α, 17α-dipropynyl-A-nor-5α-androstane-2β, 17β-dihydroxy bipropionate compound (Il) were used respectively as the active ingredients of the tablet.

As tested, the dissolution rates within 30 mins of the sample on Day 0 and the samples stored under various testing conditions of influence factors for 10 days are larger than or equal to 95%.

Example 12

Accelerating Test and Long-Term Test

According to <Guidelines for Stabilization Tests of Crude Drugs and Pharmaceutic Preparations> (Appendix XIXC, Chinese Pharmacopoeia, 2010), the samples prepared in Examples 2-11 were subjected to the accelerating test and long-term test.

The dissolution rate data of the samples in Example 2 subjected to acceleration for 6 months and long term exposure (6 months and 2 years) are shown in Table 6, Table 7 and Table 8, respectively.

Figure 6:
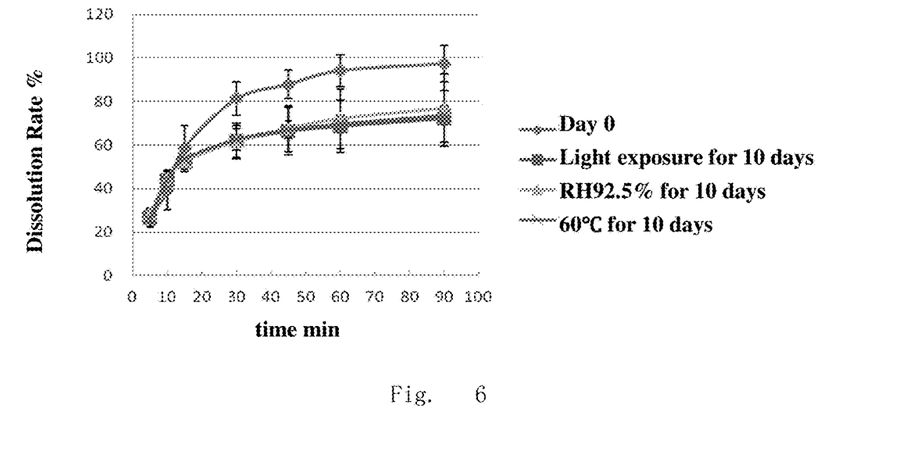
FIG. 6 shows the dissolution profile of microcrystalline cellulose-containing tablets under various conditions.

FIG. 6. Data of Dissolution Rate for the Samples Subjected to Acceleration for 6 Months.

| lot | 1 | 2 | 3 |
|---|---|---|---|
| 30 min Dissolution rate % (standard: 10 mg) | 94.13 | 95.00 | 94.64 |
| 30 min Dissolution rate % (standard: 5 mg) | 91.67 | 95.55 | 94.51 |

FIG. 7. Data of Dissolution Rate for the Samples Subjected to Long-Term (6 Month) Exposure.

| lot | 1 | 2 | 3 |
|---|---|---|---|
| 30 min Dissolution rate % (standard: 10 mg) | 92.74 | 93.77 | 94.53 |
| 30 min Dissolution rate % (standard: 5 mg) | 90.62 | 94.82 | 93.52 |

FIG. 8. Data of dissolution rate for the samples subjected to long-term (2 years) exposure.

| lot | 1 | 2 | 3 |
|---|---|---|---|
| 30 min Dissolution rate % (standard: 10 mg) | 82.4 | 82.5 | 87.24 |
| 30 min Dissolution rate % (standard: 5 mg) | 85.68 | 85.16 | 87.71 |

The results indicate that the dissolution rate of the sample prepared in Example 2 can still reach 91%-95% within 30 mins after a 6-month testing acceleration, the dissolution rate can still reach 90%-95% within 30 mins after a 6-month testing exposure, and the dissolution rate can still reach 82%-88% within 30 mins after a 2-year testing exposure. All of the samples possess good dissolubility.

The results of the accelerating test and long-term test on the samples prepared in Example 3-Example 11 show that the dissolution rate of the samples prepared in Example 3-11 may reach 90%-95% within 30 mins after a 6-month testing acceleration, the dissolution rate can still reach 90%-95% within 30 mins after a 6-month testing exposure, and the dissolution rate can still reach 82%-88% within 30 mins after a 2-year testing exposure. All of the samples possess good dissolubility.

Comparative Example 1

| Tablet comprising A-nor-5α-androstane compound and microcrystalline cellulose | |
|---|---|
| Components of the tablet | Content (g)/1000 tablets |
| A-nor-5α-androstane compound (Ia) | 50 |
| microcrystalline cellulose 101 | 540 |
| lactose | 540 |
| crospovidone | 36 |
| copovidone K30 | 24 |
| magnesium stearate | 6 |
| aerosil | 3.6 |

The A-nor-5a-androstane compound (Ia) was homogenously mixed with crospovidone, lactose and microcrystalline cellulose 101. The product was granulated with 20% (wt/v) aqueous solution of copovidone K30, half-dried at 40° C., pelletized with 20-mesh sieve and then dried. The magnesium stearate, talcum powder and the rest amount of the crospovidone in the recipe were added into the dry granules. The product was homogenously mixed and tableted for use.

Figure 5:
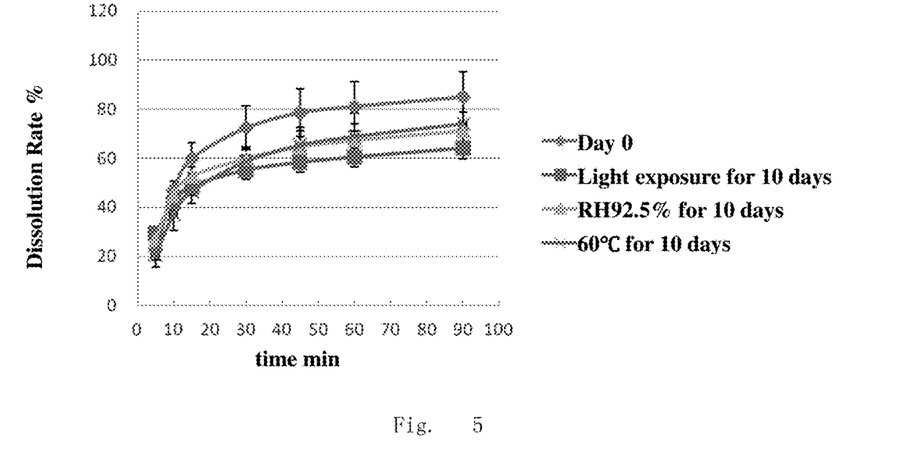
FIG. 5 shows the dissolution profile of microcrystalline cellulose-containing tablets under various conditions.

FIG. 5 shows the dissolving profiles of the sample on Day 0 and the samples stored for 10 days under the condition of influence factors (60° C., RH 92.5%, light exposure). The dissolution rate of the sample on Day 0 is lower than 75% within 30 mins. The dissolution rate of the sample stored for 10 days under the condition of influence factors (60° C., RH 92.5%, light exposure) is lower than 60% within 30 mins. The results showed that the dissolution was slowed down and limited after stored under various conditions of influence factors.

Comparative Example 2

| Tablet comprising A-nor-5α-androstane compound and microcrystalline cellulose | |
|---|---|
| Components of the tablet | Content (g)/1000 tablets |
| A-nor-5α-androstane compound (Ib) | 120 |
| microcrystalline cellulose 102 | 960 |
| CMS | 36 |
| copovidone VA64 | 60 |
| aerosil | 24 |

The A-nor-5α-androstane compound (Ia) was homogenously mixed with CMS, copovidone VA64 and microcrystalline cellulose 102 by using Equilibrium Method. The aerosil was added into the above mixture and homogenously mixed by using Equilibrium Method. The obtained powder was directly tableted for use.

FIG. 6 shows the dissolving profiles of the sample on Day 0 and the samples stored for 10 days under the condition of influence factors (60° C., RH 92.5%, light exposure). The dissolution rate of the sample on Day 0 is about 80% within 30 mins. The dissolution rate of the sample stored for 10 days under the condition of influence factors (60° C., RH 92.5%, light exposure) is about 60% within 30 mins. The results showed that the dissolution was slowed down and limited after stored under various conditions of influence factors.

Comparative Example 3

| Tablet comprising A-nor-5α-androstane compound and microcrystalline cellulose | |
|---|---|
| Components of the tablet | Content (g)/1000 tablets |
| A-nor-5α-androstane compound (Ic) | 50 |
| microcrystalline cellulose 101 | 540 |
| lactose | 828 |
| xylitol | 120 |
| mannitol | 120 |
| crospovidone | 36 |
| HPMC | 36 |
| magnesium stearate | 6 |
| aerosil | 4 |

The A-nor-5a-androstane compound (Ic) was homogenously mixed with xylitol, mannitol, lactose and microcrystalline cellulose 101. The product was granulated with 12% (wt/v) aqueous solution of HPMC, dried at 40° C. and pelletized with 20-mesh sieve. The crospovidone, magnesium stearate and aerosil were added to the dry granules, and the product was homogenously mixed, and tableted for use.

TABLE 9

Dissolubility of the formulation containing water-insoluble adjuvant microcrystalline cellulose

| Time min | Day 0 | 60° C. Day 10 | 40° C. Day 10 | Light exposure Day 10 | 60° C. Day 5 | 40° C. Day 5 | Light exposure Day 5 |
|---|---|---|---|---|---|---|---|
| 5 | 16.807 | 20.902 | 27.123 | 29.406 | 25.919 | 28.422 | 26.575 |
| 10 | 39.035 | 37.131 | 44.960 | 42.086 | 44.092 | 44.470 | 43.725 |
| 15 | 58.923 | 46.628 | 52.711 | 48.588 | 53.560 | 52.484 | 52.346 |
| 30 | 81.273 | 58.877 | 59.932 | 55.221 | 62.571 | 61.683 | 61.844 |
| 45 | 87.908 | 65.461 | 64.623 | 58.337 | 67.022 | 67.517 | 66.255 |
| 60 | 94.204 | 68.985 | 67.341 | 60.535 | 69.734 | 72.113 | 68.594 |
| 90 | 97.386 | 74.180 | 71.116 | 64.186 | 73.718 | 76.879 | 72.152 |

The dissolution rate of the samples containing water-insoluble adjuvant microcrystalline cellulose was tested after stored under different conditions. The results are shown in Table 9. For the recipe containing water-insoluble adjuvant microcrystalline cellulose, the dissolution rate of the sample at day 0 was about 80% within 30 mins, and it declined to about 60% after stored for 10 days at 40° C., and the dissolution rate declined to about 59% after stored for 10 days at 60° C. The dissolution rate decreased with the storing period under various conditions of influence factors.

It could be understood from the above experiments, the microcrystalline cellulose has a great influence on the stability and dissolution rate of the formulation. According to the formulation of the present invention, the content of the microcrystalline cellulose is preferably as low as possible (such as ≤5 wt %, preferably ≤1 wt %), and even without microcrystalline cellulose.

All documents mentioned in the present invention are incorporated herein by reference, as if each document were individually recited for reference. It is to be understood that those skilled in the art will be able to make various changes or modifications to the present invention after reading the teachings of the present invention, which also fall within the scope of the claims appended hereto.

The invention claimed is:
1. An oral formulation, wherein said oral formulation comprises an A-nor-5α androstane compound as an active ingredient, a filling agent, a disintegrant, a binder, a lubricant, and a glidant, each of which has the following parts by weight:

| active ingredient | 1-50 parts by weight |
|---|---|
| filling agent | 30-95 parts by weight |
| disintegrant | 0-20 parts by weight |
| binder | 0.1-10 parts by weight |
| lubricant | 0.1-5 parts by weight |
| glidant | 0.1-5 parts by weight | wherein said A-nor-5α-androstane compound is selected from the group consisting of:
2α, 17α-diethynyl-A-nor-5α-androstane-2β, 17β-dihydroxy compound (Ia),
2α, 17α-diethynyl-A-nor-5α-androstane-2β, 17β-dihydroxy diacetate compound (Ib),
2α, 17α-diethynyl-A-nor-5α-androstane-2β, 17β-dihydroxydipropionate compound (Ic),
2α, 17α-diethynyl-A-nor-5α-androstane-2β, 17β-dihydroxy-2β-mono succinate compound (Id),
2α, 17α-diethynyl-A-nor-5α-androstane-20, 17β-di succinate compound (Ie),
2α, 17α-diethynyl-A-nor-5α-androstane-2β, 17β-dibutyrate compound (If),
2α, 17α-dihydroxypropynyl-A-nor-5α-androstane-2β, 17β-dihydroxy compound (Ig),
2α, 17α-dicyano-A-nor-5α-androstane-2β, 17β-dihydroxy compound (Ih),
2α, 17α-diethynyl-A-nor-5α-androstane-2β, 17β-dihydroxy-di-(trichloroacetate) compound (Ii),
2α, 17α-diethynyl-A-nor-5α-androstane-2β, 17β-dihydroxy-2β-propionate-17β succinate compound (Ij),
2α, 17α-dipropynyl-A-nor-5α-androstane-2β, 17β-dihydroxy compound (Ik), and
2α, 17α-dipropynyl-A-nor-5α-androstane-2β, 17β-dihydroxy bipropionate compound (Il);
said filling agent is one or more selected from the group consisting of lactose, sorbitol, mannitol, xylitol, starch and inorganic salts;
said disintegrant is one or more selected from the group consisting of crospovidone (PVPP), croscarmellose sodium (CC Na), sodium carboxymethyl starch (CMS-Na), and low-substituted hydroxypropylcellulose (L-HPC);

said lubricant is one or more selected from the group consisting of stearic acid, sodium stearate, magnesium stearate, calcium stearate, and polyethylene glycol;
said binder is one or more selected from the group consisting of starch slurry, hydroxypropylmethylcellulose (HPMC), povidone (PVP) and copovidone (Kollidon);
said glidant is one or more selected from the group consisting of aerosil and talcum powder;
a microcrystalline cellulose in the oral formulation is present in an amount of ≤1 wt %; and
said oral formulation has one or more characteristics selected from a group consisting of:
(i) under pH5.0-8.0, the dissolution rate Y30 of A-nor-5α androstane compound in said formulation within 30 minutes is ≥80%,
(c) X3≥85%, wherein X3=Y3/$Y_{30}$; Y3 is a dissolution rate of the A-nor-5α-androstane compound in said oral formulation within 30 minutes under pH 5.0-8.0 after stored for 180 days at a temperature of 40° C.±2° C. and a relative humidity of 75%±5%, and
(d) X4≥85%, wherein X4=Y4/$Y_{30}$; Y4 is a dissolution rate of the A-nor-5α-androstane compound in said oral formulation within 30 minutes under pH 5.0-8.0 after stored for 365 days at a temperature of 25° C.±2° C. and a relative humidity of 60%±10%.

2. The oral formulation according to claim 1, wherein said oral formulation is a tablet, granule, or capsule.

3. The oral formulation according to claim 1, wherein the active ingredient, the filling agent, the disintegrant, the binder, the lubricant and the glidant have a combined weight of 90-100%, based on a total weight of the oral formulation.

4. The oral formulation according to claim 1, wherein the active ingredient, the filling agent, the disintegrant, the binder, the lubricant and the glidant have a combined weight of 100%, based on a total weight of the oral formulation.

5. The oral formulation according to claim 1, wherein the microcrystalline cellulose in the oral formulation is present in an amount of 0 wt %.

6. The oral formulation according to claim 1, wherein the oral formulation is a tablet selected from the group consisting of:

TABLE a

| Components | Content (g)/1000 tablets |
| --- | --- |
| A-nor-5α-androstane compound (Ia) | 50 |
| Lactose | 828 |
| Xylitol | 120 |
| Mannitol | 120 |
| crospovidone | 36 |
| HPMC | 36 |
| magnesium stearate | 6 |
| aerosil | 4, |

TABLE b

| Components | Content (g)/1000 tablets |
| --- | --- |
| A-nor-5α-androstane compound (Ib) | 20 |
| lactose | 1140 |
| crospovidone | 12 |
| copovidone K30 | 10 |
| magnesium stearate | 12 |
| talcum powder | 6, |

TABLE c

| Components of a tablet | Content (g)/1000 tablets |
| --- | --- |
| A-nor-5α-androstane compound (Ic) | 72 |
| mannitol | 600 |
| lactose | 390.6 |
| starch | 75 |
| CC Na | 60 |
| magnesium stearate | 1.2 |
| talcum powder | 1.2, |

TABLE d

| Components | Content (g)/1000 tablets |
| --- | --- |
| A-nor-5α-androstane compound (Id) | 600 |
| lactose | 210 |
| mannitol | 210 |
| copovidone K30 | 60 |
| magnesium stearate | 60 |
| aerosil | 60, |

TABLE e

| Components of the tablet | Content (g)/1000 tablets |
| --- | --- |
| A-nor-5α-androstane compound (Ie) | 48 |
| pregelatinized starch | 120 |
| calcium sulfate | 120 |
| sorbitol | 480 |
| CMS-Na | 240 |
| copovidone VA64 | 120 |
| polyethylene glycol | 36 |
| talcum powder | 36, |

TABLE f

| Components of the tablet | Content (g)/1000 tablets |
| --- | --- |
| A-nor-5α-androstane compound (If) | 120 |
| lactose | 720 |
| mannitol | 240 |
| HPMC | 42 |
| CC Na | 75.6 |
| aerosil | 1.2 |
| magnesium stearate | 1.2, |

TABLE g

| Components of the tablet | Content (g)/1000 tablets |
| --- | --- |
| A-nor-5α-androstane compound (Ig) | 48.8 |
| pregelatinized starch | 720 |
| mannitol | 360 |
| copovidone VA64 | 1.2 |
| L-HPC | 36 |
| aerosil | 18 |
| magnesium stearate | 16, |

TABLE h

| Components of the tablet | Content (g)/1000 tablets |
| --- | --- |
| A-nor-5α-androstane compound (Ih) | 12 |
| lactose | 660 |
| mannitol | 258 |

TABLE h-continued

| Components of the tablet | Content (g)/1000 tablets |
| --- | --- |
| sodium carboxymethylcellulose | 120 |
| copovidone VA64 | 120 |
| magnesium stearate | 18 |
| talcum powder | 12, |

TABLE i

| Components of the tablet | Content (g)/1000 tablets |
| --- | --- |
| A-nor-5α-androstane compound (Ii) | 66 |
| mannitol | 480 |
| pregelatinized starch | 240 |
| copovidone VA64 | 120 |
| crospovidone | 240 |
| magnesium stearate | 36 |
| aerosil | 18, | and

TABLE j

| Components of the tablet | Content (g)/1000 tablets |
| --- | --- |
| A-nor-5α-androstane compound | 66 |
| mannitol | 480 |
| pregelatinized starch | 240 |
| copovidone VA64 | 120 |
| crospovidone | 240 |
| magnesium stearate | 36 |
| aerosil | 18, | wherein the A-nor-5α-androstane compound in Table j) is selected from the group consisting of A-nor-5α-androstane compound (Ij), A-nor-5α-androstane compound (Ik), and A-nor-5α-androstane compound (Il).

7. A method of treating cancer in a subject in need thereof, said method comprising administering to said subject an oral formulation according to claim 1, wherein said cancer is prostate cancer or liver cancer.

8. A method of treating prostate hyperplasia, said method comprising administering to a subject an oral formulation according to claim 1.

* * * * *